(12) United States Patent
Hanke et al.

(10) Patent No.: US 7,965,812 B2
(45) Date of Patent: Jun. 21, 2011

(54) MAMMOGRAPHY SYSTEM AND OPERATING METHOD

(75) Inventors: Wilhelm Hanke, Rueckersdorf (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 74 days.

(21) Appl. No.: 12/492,510

(22) Filed: Jun. 26, 2009

(65) Prior Publication Data
US 2009/0323893 A1  Dec. 31, 2009

(30) Foreign Application Priority Data
Jun. 27, 2008  (DE) .................. 10 2008 030 698

(51) Int. Cl.
*A61B 6/04* (2006.01)
(52) U.S. Cl. ............................ 378/37; 378/21
(58) Field of Classification Search ............ 378/37, 378/21–27
See application file for complete search history.

(56) References Cited

U.S. PATENT DOCUMENTS

| 6,999,552 | B2 | 2/2006 | Tsujii | |
|---|---|---|---|---|
| 6,999,554 | B2 | 2/2006 | Mertelmeier | |
| 2008/0285712 | A1* | 11/2008 | Kopans et al. | 378/26 |

FOREIGN PATENT DOCUMENTS

| DE | 10 2006 046 741 A1 | 4/2008 |
|---|---|---|
| DE | 10 2006 048 607 A1 | 4/2008 |
| FR | 2 352 531 | 12/1977 |

* cited by examiner

*Primary Examiner* — Hoon Song
(74) *Attorney, Agent, or Firm* — Schiff Hardin LLP

(57) ABSTRACT

A mammography system has an x-ray source, a detector and a compression plate arranged in the beam path between the source and the detector. The x-ray source, the detector and the compression plate are mounted on a vertical column such that they respectively pivot around separate pivot axes. The three pivot axes are spaced apart from one another and oriented substantially parallel to one another and substantially perpendicular to a surface normal of the detector. The x-ray source and the compression plate are held on the vertical column such that they can be displaced in a plane oriented approximately vertical to their pivot axes. The mammography system is operable to obtain two sets of tomosynthesis data respectively with different tube-to-detector distances.

13 Claims, 5 Drawing Sheets

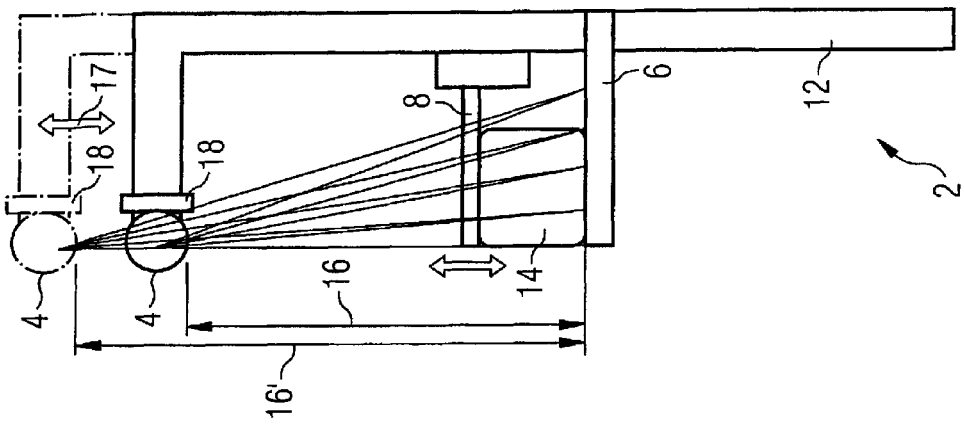
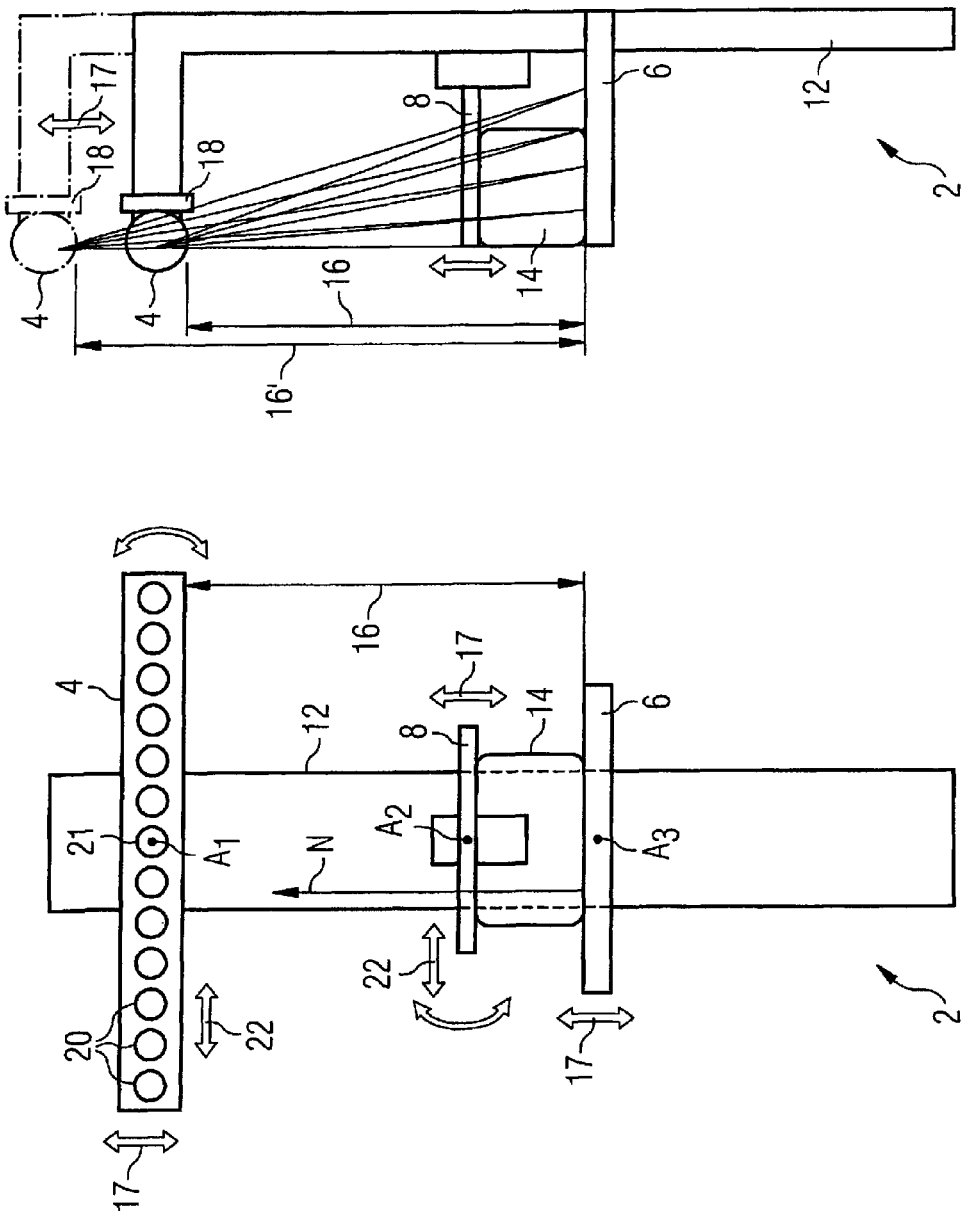

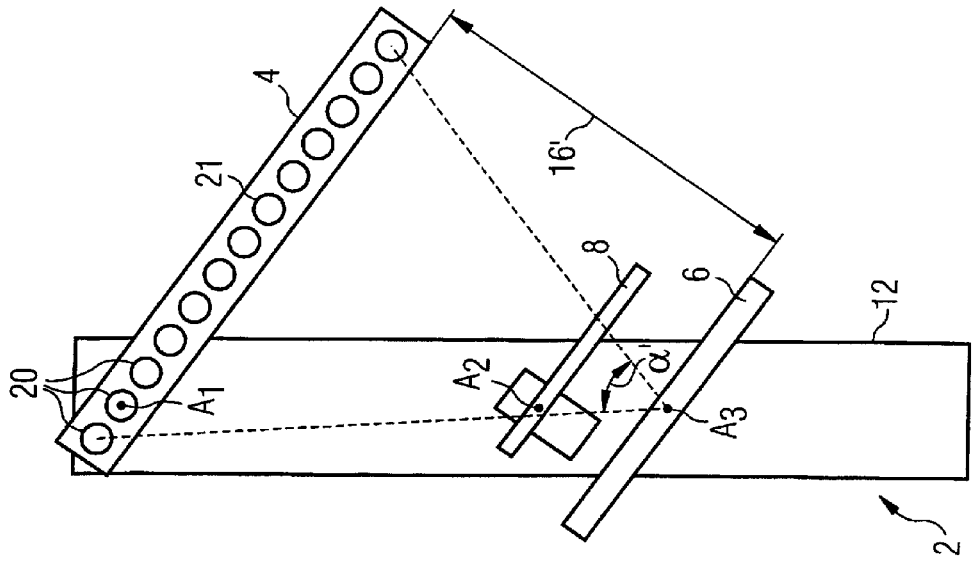
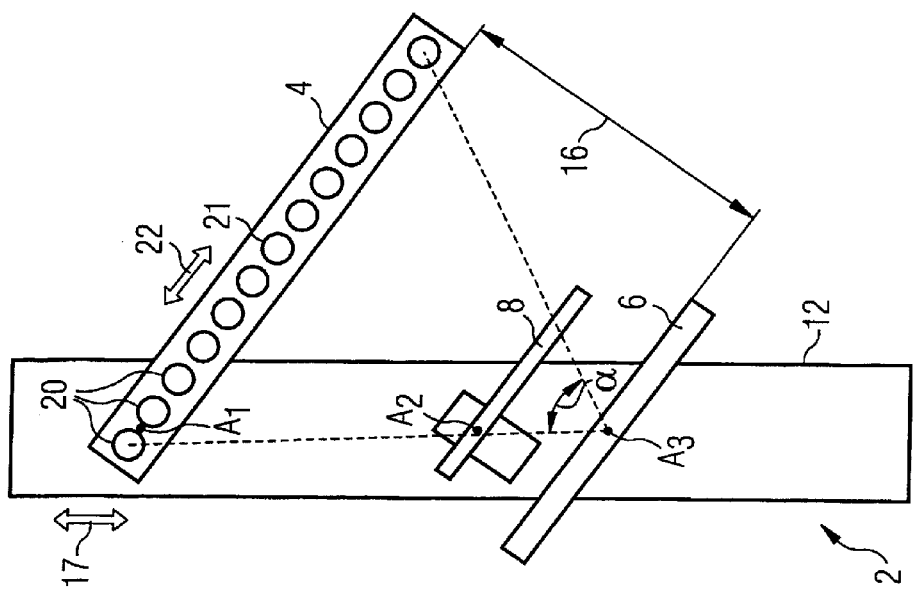

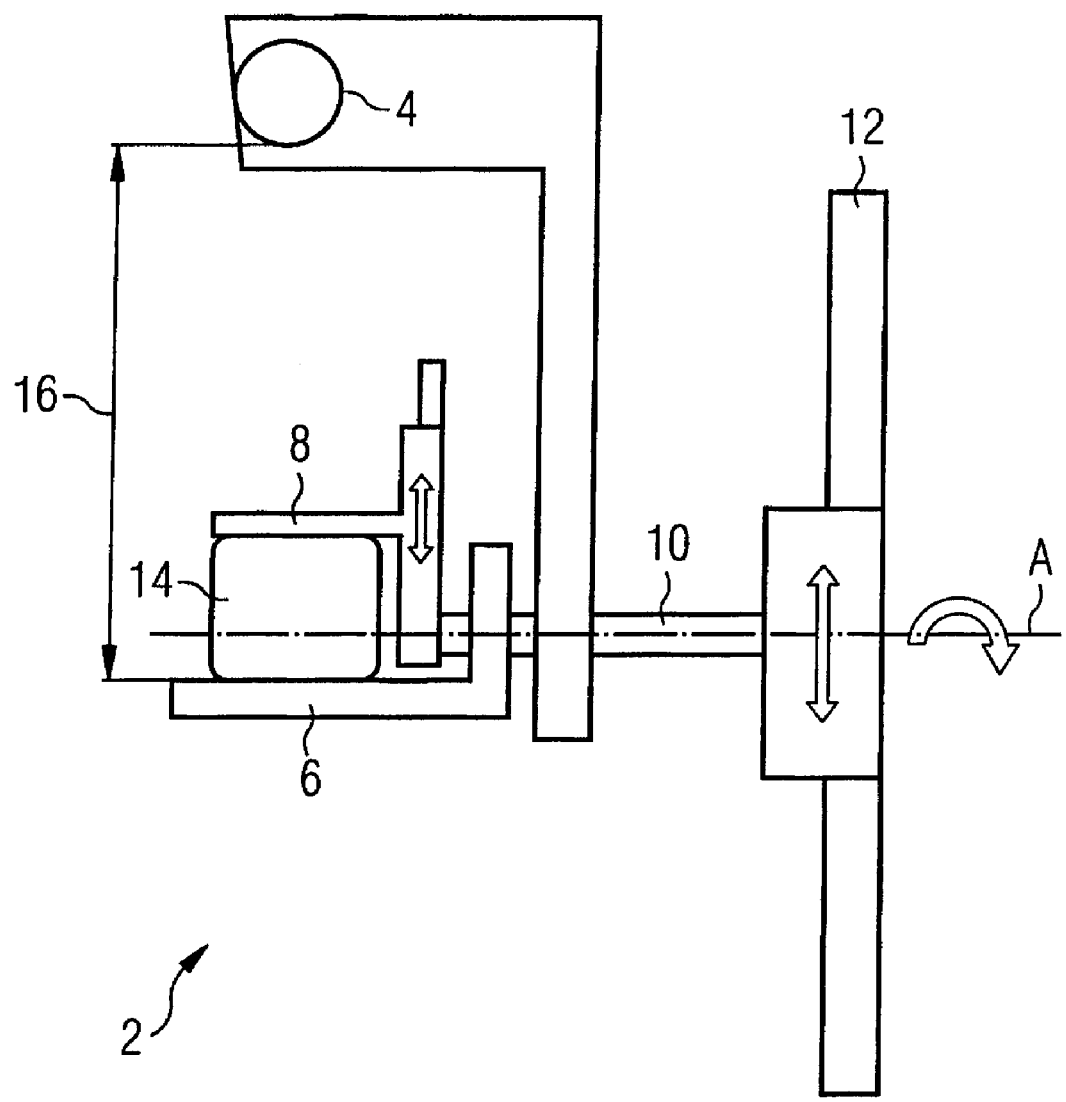

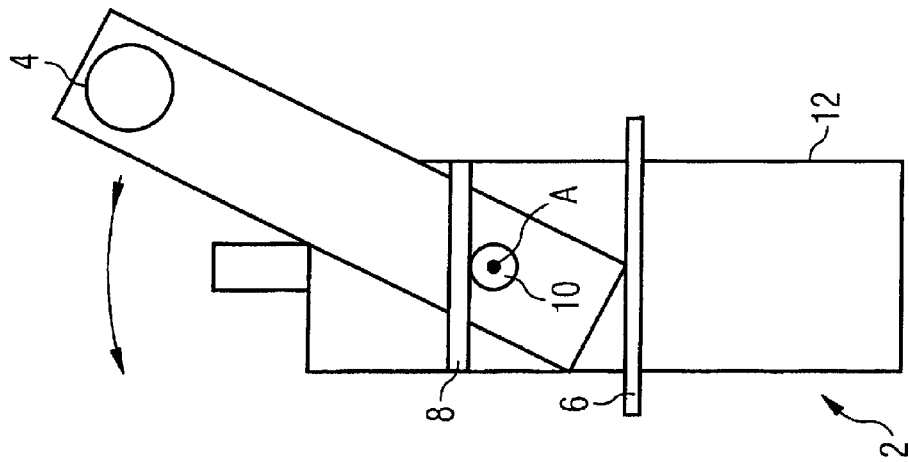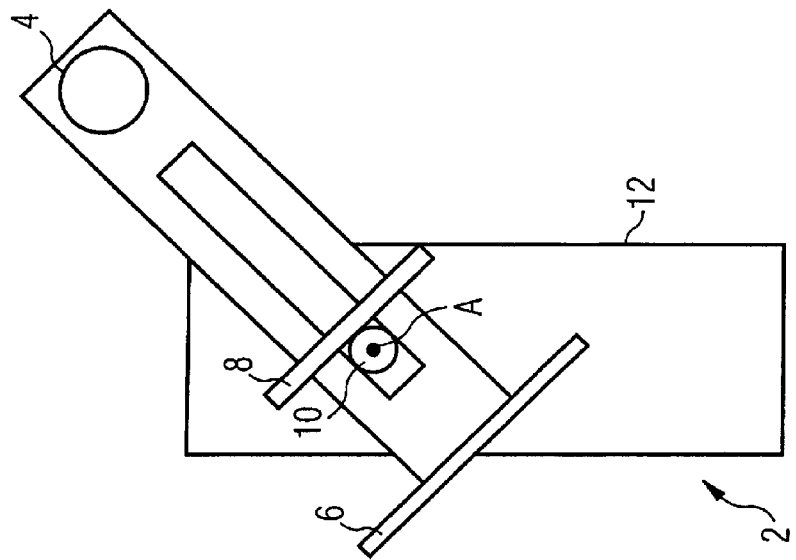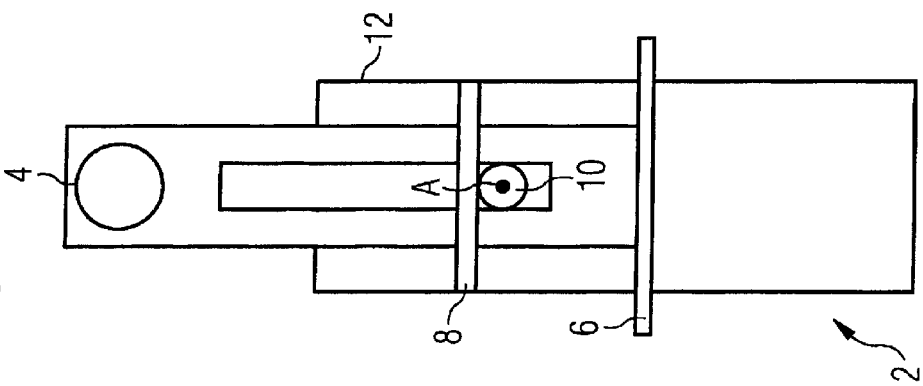

MAMMOGRAPHY SYSTEM AND OPERATING METHOD

BACKGROUND OF THE INVENTION

1. Field of the Invention

The present invention concerns a mammography system with an x-ray source, a detector and a compression plate arranged in the beam path between these, as well as a method for operation of such a mammography system.

2. Description of the Prior Art

FIG. 7 shows an example of a conventional mammography system 2. The x-ray source 4, the detector 6 and the compression plate 8 are held on a vertical column 12 by a central shaft 10. The x-ray source 4 is a commercially available x-ray tube with a tungsten rotating anode. The detector 6 comprises a bearing plate (not shown in detail) for placement of the breast 14 to be examined. X-ray source 4, detector 6 and compression plate 8 together form the measurement system of the mammography system 2 and can be rotated around a common axis A relative to the vertical column 12. The measurement system is slid along the vertical column 12 to adapt the mammography system 2 to the size of the patient to be examined. In the following a female patient is referred to, however female and male patients are always meant.

For examination the breast 14 is initially compressed; this ensues via a displacement of the compression plate 8 in the beam direction of the x-ray source 4, and said breast 14 is subsequently irradiated by a beam of x-rays. The design of mammography system 2 shown in FIG. 7 establishes the distance between the x-ray source 4 and the detector 6 (which is also designated in the following as a tube-detector distance) known as: Source-Image Distance, SID 16. The tube-detector distance SID 16 is the distance between the location of the x-ray generation and the location of the detection of the x-rays. In a conventional x-ray apparatus, this is typically the distance between the surface of the anode of the x-ray tube from which the x-ray beam used for examination emanates and the x-ray-sensitive part of the detector, for example an x-ray film. This distance is also designated as a focus-detector distance.

Mammography exposures can be produced from various directions in which the patient respective adopts a different posture. Such mammography exposures are also designated as projections. The cranio-caudal projection (CC projection) or the mediolateral-oblique projection (MLO projection) are typical. FIGS. 8 and 9 show schematic frontal views of the mammography system 2. FIG. 8 shows an example of the acquisition geometry for an MLO projection. The entire measurement system is pivoted around a central axis A to change the projections.

In addition to conventional mammography, tomosynthesis as increasingly gained importance. In this examination method the breast 14 (held stationary in a compressed state) is irradiated from different directions (projection angles). To implement a tomosynthesis it is necessary that the compression of the breast 14 is decoupled from the movement of the x-ray tube 4. FIG. 10 shows an example of the movement progression of the x-ray tube 4 during the acquisition of a tomosynthesis image data set. During the acquisition the detector 6 and the compression plate 8 stand still while the x-ray tube 4 moves.

The mechanical design is very complicated, in particular of a mammography system 2 suitable for tomosynthesis. On the one hand, a mechanically stable acquisition of the measurement system is ensured, wherein this must likewise be height-adjustable for the adaptation to the size of the patient. To adjust the various projections (for example CC or MLO projection), the measurement system must additionally be attached to the vertical column 12 such that said measurement system can rotate. If the mammography system should moreover be suitable for tomosynthesis, an additional requirement is added, namely the decoupling of the movement of detector 6 and compression plate 8 from the movement of the x-ray source 4 as a mechanical requirement.

SUMMARY OF THE INVENTION

An object of the present invention to specify a mammography system with variable acquisition geometry with simplified mechanical design, as well as an operation method for such a mammography system.

A mammography system according to the invention has an x-ray source, a detector and a compression plate arranged in the beam path between these, and moreover has the following features: the x-ray source, the detector and the compression plate are respectively held on a vertical column such that they can pivot around a separate pivot axis. The three pivot axes are spaced apart from one another and oriented at least approximately parallel to one another and at least approximately perpendicular to a surface normal of the detector. The x-ray source and the compression plate are held on the vertical column such that they can be displaced in a plane oriented approximately vertical to their pivot axes.

The mammography system with the cited features is significantly simplified in design relative to conventional mammography systems. Instead of a common shaft which must bear the load of the complete measurement system (x-ray source, detector, compression plate), a separate shaft is used for each module of the measurement system. For this reason it is possible to design both the bearing shaft itself and the associated adjustment mechanism for a lower mechanical load. In conventional mammography systems, the entire mass of the measurement system is rotated around a single axis given a change of the projection (for example from CC projection to MLO projection). High torques arise on the pivot axis given such a rotation movement. Given a manual change of the projection, the high torques stress the assisting personnel; if the change occurs automatically, high torques must be accepted by the adjustment mechanism. Given a mammography system with the cited features, the individual components of the measurement system are borne separately. The change of the projection ensues via separate movement of the modules of the measurement system. Due to the comparably smaller mass that is moved, the incident torques are likewise significantly lower. The operator or a motorized adjustment mechanism that may be used is unburdened.

A variation of the tube-detector distance, that is desirable for multiple reasons, is achieved according to a first embodiment in that the x-ray source is held on a vertical column such that said x-ray source can be displaced in a longitudinal direction that essentially points in the direction of the length direction of the vertical column. A variation of the tube-detector distance allows the dose used for image generation to be varied.

To change the projection, the detector, the compression plate and the x-ray source are pivoted around their respective axes. After such a pivoting process, the individual components of the measurement system are arranged offset laterally from one another relative to a surface normal of the detector. This offset is compensated by a corresponding transverse displacement of compression plate and x-ray source. According to an additional embodiment, the x-ray source and/or the compression plate are additionally held on the vertical column such that they can be displaced in a transversal direction different from the longitudinal direction. The transverse direction is oriented essentially perpendicular to the pivot axis of the x-ray source or, respectively, of the compression plate. In other words: the displacement movement of the x-ray source and/or of the compression plate is composed of a displacement in the longitudinal direction and/or a displacement in a transversal direction differing from this.

Given a variation of the acquisition geometry (for example from a CC projection to an MLO projection), the tube-detector distance (SID) varies for geometric reasons. This unwanted effect is compensated in that the x-ray source is moved in the longitudinal direction. A transverse offset that arises in turn due to this correction in the longitudinal direction is compensated via a repeated movement in the transverse direction.

Essentially two different designs are conceivable in order to achieve the movement possibilities for the x-ray source and the compression plate that are presented above.

A first possibility according to one embodiment is that the x-ray source and/or the compression plate is held on the vertical column such that it can be displaced together with its pivot axis in the longitudinal direction. In other words: the x-ray source and/or the compression plate is attached to the vertical column such that its pivot axis follows the displacement in the longitudinal direction but not a displacement in the transversal direction. According to an additional possibility and embodiment, the x-ray source and/or the compression plate is held on the vertical column such that it can be displaced together with its pivot axis in the longitudinal direction and in the transverse direction. In other words: the pivot axis follows both a displacement in the longitudinal direction and a displacement in the transverse direction.

In addition to classical mammography, tomosynthesis has gained increasing importance as an examination method. Therefore, according to an additional embodiment the x-ray source is formed in the manner of an array of a number of individual x-ray emitters. With the use of such a multi-focus x-ray source it is possible to irradiate the breast to be examined from a number of different projection directions without the x-ray source itself having to be moved. For this purpose, the individual x-ray emitters (arranged approximately in parallel) are activated in succession and excited to emission. The tomosynthesis examination can be significantly accelerated via the use of such a multifocus x-ray tube. A particularly suitable x-ray source that comprises a plurality of individual x-ray emitters additionally possesses a cold field emission cathode based on carbon nanotubes. Cathodes based on carbon nanotubes use these as a field emitter; the cathode therefore does not need to be heated, which is in particular advantageous for an x-ray source that comprises a plurality of individual x-ray emitters. In comparison to other field emitters (for example fine metal spikes), carbon nanotubes are comparably robust.

The use of a multifocus x-ray tube is particularly advantageous in combination with a variable tube-detector distance (SID) since the tomosynthesis angle can be varied via a variation of the SID. If a variation of the SID were not possible, the tomosynthesis angle could be varied only by exchanging the x-ray source. This would have to be exchanged for a different, elongated x-ray source. However, such an exchange is very complicated. The conversion of the mammography system can advantageously be avoided due to the variability of the SID.

A variation of the SID allows the imaging dose to be varied without the x-ray power needing to be varied. This is particularly advantageous when the imaging dose should be increased but is limited by the power of the x-ray source. In this case the SID can be reduced (meaning that the tomosynthesis angle is increased) and thus the imaging dose can be increased.

A variation of the SID allows a double tomosynthesis scan. The breast is initially scanned at a first tube-detector distance and is subsequently scanned at a second tube-detector distance different from the first. In this way the scan density can be increased so that x-rays which irradiate the breast from different directions can be taken into account for the image reconstruction. In this case an increase in additional focal paths is also spoken of. Due to the additional information acquired as a result of the variation of the SID, the depth resolution of the breast can be improved; occurring artifacts that are unavoidable in tomosynthesis are reduced.

Given a variation of the acquisition geometry (for example from a CC projection to an MLO projection), the SID likewise changes for geometric reasons. The tomosynthesis angle also varies together with the variation of the SID. In order to compensate for this (possibly unwanted) effect, it is advantageous when the x-ray source can be adjusted in one direction that approximately corresponds to the length extent of the vertical column. Due to the adjustment of the x-ray source, the SID (and thus also the tomosynthesis angle) can be adjusted again to the original value.

To adapt the mammography system to the size of the examined patient (who normally is standing), according to a further embodiment the x-ray source, the detector and the compression plate can be displaced together in the longitudinal direction.

The mammography system can in particular be designed so that, given an adaptation to the size of the patient (given which essentially the bearing plate integrated into the detector is displaced in terms of its height), the other components of the measurement system are correspondingly simultaneously moved. The handling of the mammography system can thus be improved.

Accordingly, at least one first tomosynthetic image data set is acquired at a first tube-detector distance; a second tomosynthetic image data set is acquired at a second tube-detector distance differing from the first. The acquisition of two different tomosynthesis image data sets from respective different tube-detector distances allows additional image information to be acquired, and possibly allows the image data sets acquired from the different tube-detector distances to be combined one another. Due to the additional scanning of the breast with an additional tube-detector distance, artifacts occurring in the tomosynthesis that are caused by the inherently incomplete scanning are reduced.

BRIEF DESCRIPTION OF THE DRAWINGS

FIG. 1 is a front view of a mammography system in accordance with the present invention.

FIG. 2 is a side view of the mammography system of FIG. 1.

FIGS. 3, 4, 5 and 6 are further front views of the mammography system in accordance with the present invention.

FIG. 7 is a sectional view of the mammography system in accordance with the present invention.

FIGS. 8, 9, and 10 are front views of a known mammography system.

DESCRIPTION OF THE PREFERRED EMBODIMENTS

Figure 5:
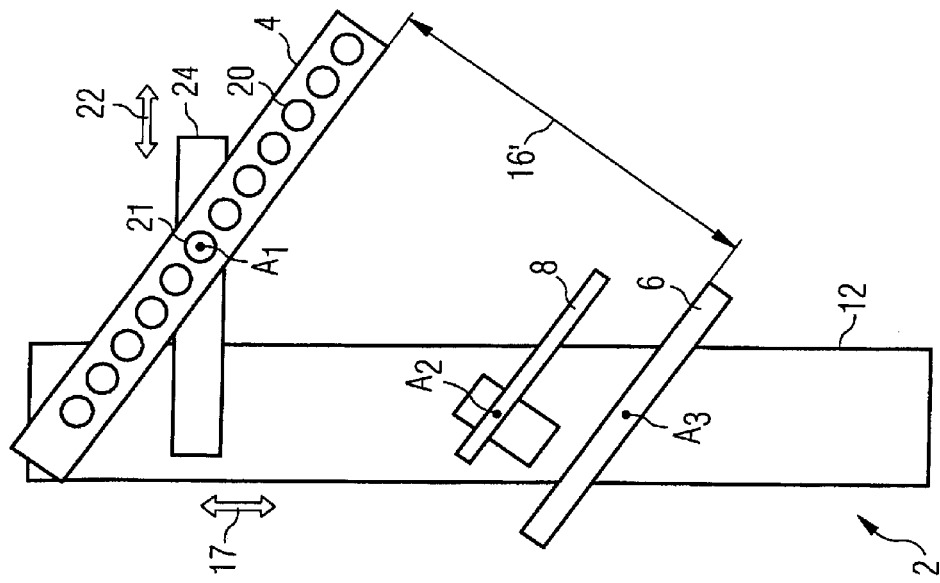

FIG. 1 shows a mammography system 2 at whose vertical column 12, an x-ray source 4, a detector 6 and a compression plate 8 are attached. The detector 6 simultaneously serves as a bearing plate for the placement of the breast 14. The x-ray source 4, the detector 6 and the compression plate 8 together form the measurement system of the mammography system 2, and each module is separately attached to the vertical column 12 such that it can pivot on an axis $A_1$-$A_3$. In order to enable a compression of the breast 14, the compression plate 8 is held on the vertical column 12 such that it can be displaced in a longitudinal direction 17 that is essentially oriented in the length direction of the vertical column 12. The same applies to the x-ray source 4. A displacement of the x-ray source 4 in a longitudinal direction 17 that is essentially oriented in the length direction of the vertical column 12 allows mammography acquisitions with differing tube-detector distance (SID) 16.

FIG. 2 shows a schematic side view of the mammography system 2 given two different tube-detector distances 16, 16'. The x-ray source 4 is mounted on a rail 18 that allows a displacement of the x-ray source 4 in a transversal direction 22 shown in FIG. 1. The compression plate 8 and the detector 6 can also be held at the vertical column 6 such that they can be displaced in a transversal direction 22. A displacement of these modules in the transversal direction 22 can ensue with the aid of a suitable rail, just as this is shown for the x-ray source 4. The possibility of such a displacement is discussed in detail further below.

Depending on whether the mammography system 2 should be used for acquisition of conventional mammograms or for acquisition of tomosynthesis image data sets, the x-ray source 4 is either a conventional x-ray tube or a multifocus tube which consists of a plurality of individual x-ray emitters 20.

A mammography system 2 for acquisition of tomosynthesis image data sets is shown in FIG. 1 through 6. The shown x-ray source 4 possesses a plurality of individual x-ray emitters 20 that are arranged next to one another in the manner of an array. The x-ray emitters 20 advantageously possess a cold field emission cathode based on carbon nanotubes. In the event that the mammography system 2 should be used for the acquisition of conventional mammograms, a conventional x-ray tube (omitting all remaining x-ray emitters 20) is installed at the position of the x-ray emitter 21 located near the pivot axis $A_1$ in FIG. 1.

FIG. 1 shows the mammography system 2 in a position that allows the acquisition of a CC projection. A pivot movement of all three components of the measurement system around their respective pivot axes $A_1$ through $A_3$ ensues to change the projection. Since the individual components of the measurement system are laterally offset against one another relative to the normal N of the detector after such a pivot movement, the x-ray source 4 and the compression plate 8 are respectively slid in a transversal direction 22. This transversal direction 22 runs approximately in a plane perpendicular to the respective pivot axis $A_1$, $A_2$ of the x-ray source 4 or, respectively, of the compression plate 8. In the event that it is necessary, a displacement of the detector 6 corresponding to the displacement of the compression plate 8 and of the x-ray source 4 can likewise ensue in the transversal direction 22 so that the offset caused relative to the normal N by the pivot movement of the individual components can be compensated.

The result of the pivot process and the subsequently transversal displacement is shown in FIG. 3. After a pivot process of the measurement system, the mammography system 2 is located in a position for the implementation of a mammography in MLO projection. In principle, the measurement system can be set to arbitrary projections as long as its components no longer collide with one another. To vary the acquisition angle of the detector 6, it is advantageously merely rotated on its pivot axis $A_3$; in contrast to this, the compression plate 8 and the x-ray source 4 are moved rotated on their axes $A_2$, $A_3$ and moved in the transversal direction 22.

As a result of the pivot process of the measurement system, the distance between the x-ray source 4 and the detector 6 (the tube-detector distance, SID 16) varies. The tomosynthesis angle α also varies due to the variation of the SID 16. This sometimes unwanted effect is compensated in that the x-ray source 4 is moved in the longitudinal direction 17 along the vertical column 12.

FIG. 4 shows the mammography system 2 given a now-greater SID 16'. corresponding to the larger SID 16', the tomosynthesis angle α' is smaller than at the position shown in FIG. 3.

Figure 6:
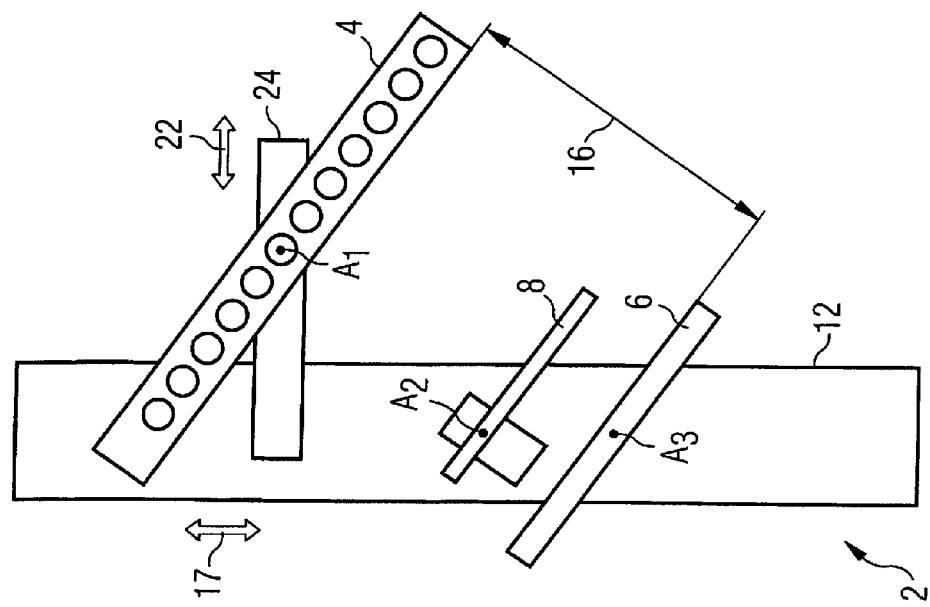

FIGS. 5 and 6 show an additional exemplary embodiment of a mammography system 2. Like the mammography system 2 in FIGS. 3 and 4, this is located in a position for acquisition of an MLO projection. In contrast to the mammography system 2, shown in FIGS. 3 and 4, the x-ray source 4 is now attached to a boom arm 24. This allows a movement of the x-ray source 4 in the transversal direction 22, which is now oriented nearly perpendicular to the length direction of the vertical column 12. The x-ray source 4 is attached to the boom arm 24 so that its pivot axis 241 follows the displacement in the transversal direction 22. In contrast to this, in the mammography system 2 shown in FIGS. 2 and 4, the pivot axis $A_1$ follows only the displacement movement in the longitudinal direction 17 but not that in the transversal direction 22.

Given the mammography system 2 shown in FIGS. 5 and 6 it is also possible to vary the SID 16. Here the variation of the SID 16, 16' also ensues via a displacement of the x-ray source 4 in the longitudinal direction 17.

The variation of the SID 16, 16' allows a particular operating method for a mammography system 2 according to any of the addressed exemplary embodiments. In this operating method, a first tomosynthetic image data set is generated at a first SID 16 (see FIG. 3 or 5) and a second tomosynthetic image data set is generated at a second SID 16' (see FIG. 4 or 6). The two tomosynthetic image data sets can be individually or can subsequently be combined into a joint image data set.

Although modifications and changes may be suggested by those skilled in the art, it is the intention of the inventors to embody within the patent warranted hereon all changes and modifications as reasonably and properly come within the scope of their contribution to the art.

We claim as our invention:

1. A mammography system comprising:
   an x-ray source that emits a radiation beam in a beam path;
   a radiation detector;
   a compression plate located in said beam path between said x-ray source and said radiation detector, said compression plate being configured to compress a breast being irradiated by said x-rays;
   a vertical column;
   an x-ray source mount that mounts said x-ray source to said vertical column allowing pivoting of said x-ray source around a first pivot axis;
   a compression plate mount that mounts said compression plate to said vertical column allowing pivoting of said compression plate around a second pivot axis;
   a radiation detector mount that mounts said radiation detector to said vertical column allowing pivoting of said radiation detector around a third pivot axis;
   said first, second and third pivot axes being separate and spaced apart from each other and oriented substantially parallel to each other and substantially perpendicular to a surface normal of said detector; and said x-ray source mount being configured to displace said x-ray source in a plane oriented substantially vertical to said first pivot axis, and said compression plate mount being configured to allow displacement of said compression plate in a plane oriented substantially vertically to said third pivot axis.

2. A mammography system as claimed in claim 1 wherein said x-ray source mount is configured to allow displacement of said x-ray source in a longitudinal direction substantially coinciding with a vertical direction of said vertical column.

3. A mammography system as claimed in claim 2 wherein said x-ray source mount is configured to allow displacement of said x-ray source in a transverse direction, differing from said longitudinal direction, said transverse direction being oriented substantially perpendicularly to said first pivot axis.

4. A mammography system as claimed in claim 3 wherein said x-ray source mount is configured to allow displacement of said x-ray source in said longitudinal direction together with corresponding displacement of said first pivot axis.

5. A mammography system as claimed in claim 3 wherein said x-ray source mount is configured to allow displacement of said x-ray source in said longitudinal direction and in said transverse direction together with corresponding displacement of said first pivot axis in each of said longitudinal direction and said transverse direction.

6. A mammography system as claimed in claim 1 wherein said compression plate mount is configured to allow displacement of said compression plate in a longitudinal direction substantially coinciding with a vertical direction of said vertical column, and to allow displacement of said compression plate in a transverse direction, different from said longitudinal direction, said transverse direction being oriented substantially perpendicular to said third pivot axis.

7. A mammography system as claimed in claim 6 wherein said compression plate mount is configured to allow displacement of said compression plate in said longitudinal direction together with corresponding displacement of said third pivot axis.

8. A mammography system as claimed in claim 6 wherein said compression plate is configured to allow displacement of said compression plate in said longitudinal direction and in said transverse direction together with corresponding displacement of said third pivot axis in each of said longitudinal direction and said transverse direction.

9. A mammography system as claimed in claim 1 wherein said x-ray source mount, said radiation detector mount and said compression plate mount are configured to allow displacement together of said x-ray source, said radiation detector and said compression plate in a longitudinal direction substantially coinciding with a vertical direction of said vertical mount.

10. A mammography system as claimed in claim 1 wherein said x-ray source comprises an array of a plurality of individual x-ray emitters.

11. A mammography system as claimed in claim 10 wherein at least one of said x-ray emitters comprises a carbon nanotube-based cold field emission cathode.

12. A method for operating a mammography system comprising an x-ray source, a radiation detector, a compression plate, and a vertical column to which said x-ray source and said radiation detector are mounted with said compression plate mounted to said vertical column therebetween, said method comprising the steps of:
　mounting said x-ray source to said vertical column to allow pivoting of said x-ray source around a first pivot axis, mounting said compression plate to said vertical column allowing pivoting of said compression plate around a second pivot axis;
　mounting said radiation detector to said vertical column allowing pivoting of said radiation detector around a third pivot axis, said first, second and third pivot axes being separate and spaced apart from each other and oriented substantially parallel to each other and substantially perpendicular to a surface normal of said detector;
　selectively displacing said x-ray source in a plane oriented substantially vertically to said first pivot axis, and selectively displacing said compression plate in a plane oriented substantially vertically to said third pivot axis to selectively vary a spacing between a focus of the x-ray source and a detector surface of the radiation detector, which defines a tube-detector distance; and
　compressing a breast between said compression plate and said irradiation detector while irradiating the breast with x-rays emitted from said x-ray source to acquire a first set of tomosynthetic data from the compressed breast by irradiating the compressed breast with a first tube-detector distance, and to acquire a second set of tomosynthetic data from the compressed breast by irradiating the compressed breast with a second tube-detector distance differing from said first tube-detector distance.

13. A method as claimed in claim 12 comprising, in a processor, electronically reconstructing an image of the compressed breast from said first set of tomosynthetic image data and said second set of tomosynthetic image data.

\* \* \* \* \*